United States Patent [19]
Ezzell et al.

[11] Patent Number: 5,744,574
[45] Date of Patent: Apr. 28, 1998

[54] ISOMALEIMIDES AND POLYMERS DERIVED THEREFROM

[75] Inventors: Stephen A. Ezzell, Woodbury; Richard G. Hansen, St. Paul; Gregory J. Anderson, Brooklyn Park, all of Minn.

[73] Assignee: Minnesota Mining and Manufacturing Company, St. Paul, Minn.

[21] Appl. No.: 557,086

[22] PCT Filed: Dec. 5, 1995

[86] PCT No.: PCT/US95/15885

§ 371 Date: Dec. 5, 1995

§ 102(e) Date: Dec. 5, 1995

[87] PCT Pub. No.: WO97/20832

PCT Pub. Date: Jun. 12, 1997

[51] Int. Cl.$^6$ .......................... C08G 69/08; C07D 307/02
[52] U.S. Cl. .......................... 528/315; 528/318; 549/475; 549/480
[58] Field of Search .......................... 528/315, 318; 549/475, 480

[56] References Cited

U.S. PATENT DOCUMENTS

| | | |
|---|---|---|
| 2,980,701 | 4/1961 | Sauers et al. |
| 2,995,577 | 8/1961 | Sauers et al. |
| 2,998,429 | 8/1961 | Sauers et al. |
| 3,035,065 | 5/1962 | Sauers et al. |
| 3,041,376 | 6/1962 | Sauers et al. |
| 3,144,435 | 8/1964 | Sauers et al. |
| 3,232,763 | 2/1966 | Burness et al. |
| 3,631,005 | 12/1971 | Fan. |
| 4,179,444 | 12/1979 | Roth. |
| 4,581,461 | 4/1986 | Rossi et al. |
| 4,732,963 | 3/1988 | Wank et al. |
| 4,782,133 | 11/1988 | deKoning et al. |
| 5,079,338 | 1/1992 | Schenach et al. ................ 528/345 |
| 5,082,920 | 1/1992 | Harper ................ 528/205 |

FOREIGN PATENT DOCUMENTS

| | | |
|---|---|---|
| 0 135 964 | 9/1964 | European Pat. Off. |
| 0 250 248 | 6/1987 | European Pat. Off. |

OTHER PUBLICATIONS

Imai, et al., J. Poly. Sci., Poly. Chem., 13, 1691–1698 (1975).
Cotter et al., J. Org. Chem., 26(1) 10–15 (1961).
Nagarathinam et al., Polymer Bulletin 16, 147–151 (1986).
Nagarathinam et al.., J. Macromol. Sci.–Chem., A25(12), pp. 1675–1682 (1988).
Nagarathinam, et al., British Polymer Journal 22 (1990) 351–356.
Chisholm, et al., Polymer, 1992, vol. 33, No. 4.
Fan, Macromolecule, vol. 9, No. 1, Jan–Feb 1976.
Jacovic et al., Polymer Engineering & Science, August 1985, vol. 25, 12.
Ueda, et al., Journal of Polymer Science, Polymer Chem. Edition, vol. 13, 2735–2740 (1975).
Rajeswari, et al., Indian Journal of Chemistry, vol. 28A, Nov. 1989, pp. 965–968.
Nagarathinam, et al., Polymer Journal, vol. 18, No. 11, pp. 865–869 (1986).
Pyriadi et al., Arab Gulf J. Scient. Res. Math Phys. Sci., A5(3), pp. 341–348 (1987).

*Primary Examiner*—John M. Cooney, Jr.
*Attorney, Agent, or Firm*—Lorraine R. Sherman

[57] ABSTRACT

Isomaleimides and polyisomaleimides can be prepared by a method comprising the steps in sequence: admixing a maleamic acid or polymaleamic acid with an acid halide, reacting the admixture with a tertiary amine at a temperature sufficiently low to suppress the formation of a maleimide, and isolating the resulting isomaleimide or polyisomaleimide. Polymerization of a polyisomaleimide with a polynucleophilic monomer (polythiol, polyol, polyamine) produces novel polymers.

23 Claims, No Drawings

ISOMALEIMIDES AND POLYMERS DERIVED THEREFROM

FIELD OF THE INVENTION

This invention relates to isomaleimides and polyisomaleimides, a method of preparation thereof, and polymers (i.e., polymaleamides) obtained therefrom. Polymaleamides of the invention find use as adhesives, sealants, molding compounds, protective coatings, binders for abrasives, potting compounds, and crosslinking agents for hybrid materials systems. Isomaleimides and polyisomaleimides of the invention find use as surface-active agents.

BACKGROUND OF THE INVENTION

Ambient-curable polymeric materials having useful properties are in constant demand in the chemical industry. For many years, polyurethanes have filled this need, and their pervasiveness in commerce is testimony to their versatility and utility. However, polyurethanes are prepared from polyisocyanates, materials that have become increasingly regulated.

Isomaleimides and bis(isomaleimides) are known. They are generally obtained from the reaction of amines with maleic anhydride to form a maleamic acid, followed by cyclic dehydration of the maleamic acid to form an isomaleimide. While the formation of maleamic acids is relatively straightforward, the subsequent cyclic dehydration procedures disclosed in these references sometimes require expensive reagents and/or conditions that do not always provide high yields of pure isomaleimides. In particular, it is known that acids, bases, and heat catalyze the isomerization of isomaleimides to maleimides, and that thermodynamically-favored maleimide is often isolated in preference to the kinetically-favored isomaleimide.

Known low molecular weight, non-polymeric bis (isomaleimides) are all crystalline solids. Therefore, when used in reactions subsequent to their isolation, these solid materials must be taken up in a solvent whose cleanup and disposal may be difficult, expensive, and/or hazardous.

Polymers derived from non-polymeric bis (isomaleimides) are known. They have been obtained by the reaction of suitable bis(isomaleimides) with primary or secondary diamines to produce polymaleamides or with dihydric phenols to produce poly (half-ester half-maleamides). All of the diamine polymerization reactions described were carried out in an organic solvent or diluent.

SUMMARY OF THE INVENTION

Briefly, this invention provides a novel method for the preparation of isomaleimides and polyisomaleimides comprising the steps, in sequence:
(a) admixing at least one of a maleamic acid and polymaleamic acid with an acid halide,
(b) reacting the resulting admixture with a tertiary amine at a temperature sufficiently low to suppress the formation of a maleimide, and
(c) isolating the resulting isomaleimide or polyisomaleimide.

"Polyisomaleimide" means a molecule having two or more isomaleimide functionalities.

A maleamic acid or a polymaleamic acid, reactants in this method, can be prepared, as is known in the art, by reacting a compound comprising one or more primary amine groups with maleic anhydride. It is understood that because the primary amine can be polymeric or nonpolymeric, the terms "polyamine," "polymaleamic acid," and "polyisomaleimide" also encompass "polymeric polyamine," "polymeric polymaleamic acid," and "polymeric polyisomaleimide," respectively.

In yet another aspect, the invention provides novel polyisomaleimides of the general formula (1):

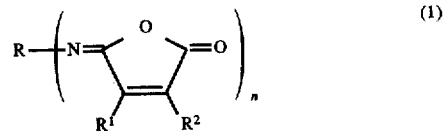

wherein R represents a polyvalent organic group derived from a polymeric primary polyamine by replacement of both hydrogen atoms from each amino group for each isomaleimide group formed, and
$R^1$ and $R^2$ are the same or different and are independently selected from the group consisting of hydrogen, $C_1$ to $C_{20}$ linear, branched or cyclic aliphatic groups, $C_6$ to $C_{20}$ aromatic groups (e.g., phenyl, naphthyl, benzyl), fluorine, chlorine, bromine, and iodine, or $R^1$ and $R^2$ may be joined together to form a cyclic ring that may be aromatic or alicyclic;
n represents the degree of isomaleimide functionality, and is an integer of at least 2, preferably from 2 to about 50,000, more preferably from 2 to 5000, most preferably from 2 to 100, and even more preferably from 2 to 10.

In a preferred embodiment, R represents a divalent organic group derived from a compound having two primary amine groups, $R^1$ and $R^2$ are hydrogen, and n is 2.

Preferably, polymeric polyisomaleimides of the invention are liquids at ambient temperatures (i.e., approximately 20°–23° C.).

In yet a further aspect, this invention provides polymeric isomaleimides of the general formula (1')

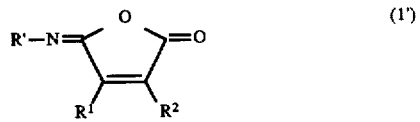

wherein R' represents an organic group derived from a polymeric primary amine by replacement of both hydrogen atoms from the amino group for the isomaleimide group formed, and $R^1$ and $R^2$ are as defined above.

In a further aspect, the invention provides novel polymers prepared by the polymerization reaction of a liquid polymeric polyisomaleimide of formula 1 with a polynucleophilic primary or secondary polyamine, polynucleophic non-phenolic polyol, or polynucleophilic polythiol monomer, or combination thereof, to form a polymaleamide or a polymer composition comprising a half ester of a polymaleamide, or a half thioester of a polymaleamide. Preferably, the nucleophilic monomer is an amine comprising at least two primary amine groups, an amine comprising at least two secondary amine groups, an amine comprising at least one primary amine group and at least one secondary amine group, a polyol comprising two or more —OH groups, or a thiol comprising two or more —SH groups. In a preferred embodiment, the invention provides a method of preparing a polymer by the polymerization reaction of liquid polymeric polyisomaleimides and a polymeric polynucleophilic monomer at ambient temperature in the absence of organic diluents or solvents. Preferably, the polynucleophilic monomer is a liquid or is soluble in the polymeric polyisomaleimide.

Such polymers can comprise structural units of the formula

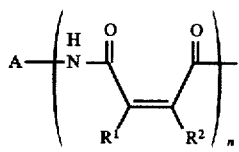

wherein A is any polyvalent polymeric organic group which can be an aliphatic, alicyclic, or aromatic group including, but not limited to hydrocarbon groups such as alkylene, cycloalkylene, alkenylene, alkynylene, arylene, aralkylene, and alkarylene groups, and can include 0 to 100 heteroatoms that interrupt carbon chains, the heteroatoms including, but not limited to, nitrogen, sulfur, non-peroxidic oxygen, phosphorous, silicon, and combinations thereof, to form, e.g., ether, thio, or amino linkages, which groups optionally can contain substituent groups, so long as A and its substituent groups do not interfere with formation of isomaleimides, polyisomaleimides, or polymers of the invention, and $R^1$ and $R^2$ are as previously defined, and n is an integer representing the degree of functionality of A, having a value previously defined.

Such polymers preferably comprise structural units of the formula

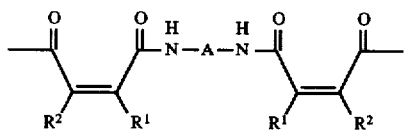

wherein —HN—A—NH— is a polyvalent polymeric group derived from a primary polyamine by removal of at least one hydrogen atom from each primary amine group, and $R^1$, $R^2$, and A are as previously defined.

In another embodiment, polymers of the invention have the general formula

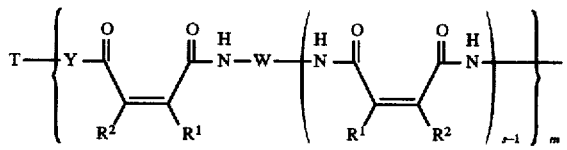

wherein Y is independently —NH—, —O—, or —S—,

W is any polyvalent organic group including aliphatic, alicyclic, and aromatic groups, including, but not limited to hydrocarbon groups such as alkylene, cycloalkylene, alkenylene, alkynylene, arylene, aralkylene, and alkarylene groups, and can include 0 to 100 heteroatoms that interrupt carbon chains, the heteroatoms including, but not limited to, nitrogen, sulfur, non-peroxidic oxygen, phosphorous, silicon, and combinations thereof, to form, e.g., ether, thio, or amino linkages, which groups optionally can contain substituent groups, so long as W and its substituent groups do not interfere with formation of isomaleimides, polyisomaleimides, or polymers of the invention, T is any polyvalent polymeric organic group including aliphatic, alicyclic, and aromatic groups, including, but not limited to hydrocarbon groups such as alkylene, cycloalkylene, alkenylene, alkynylene, arylene, aralkylene, and alkarylene groups, and can include 0 to 100 heteroatoms that interrupt carbon chains, the heteroatoms including, but not limited to, nitrogen, sulfur, non-peroxidic oxygen, phosphorous, silicon, and combinations thereof, to form, e.g., ether, thio, or amino linkages, which groups optionally can contain substituent groups, so long as T and its substituent groups do not interfere with polymers of the invention, $R^1$ and $R^2$ are as previously defined, and s and m independently are integers representing the degree of functionality of W and T, respectively, s and m independently are integers of 2 or greater, preferably 2 to about 1000, more preferably 2 to about 100, and most preferably 2 to about 10.

Such polymers preferably comprise repeating units of the formula

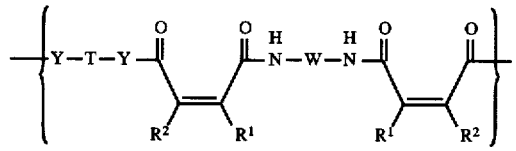

wherein W, T, Y, $R^1$, and $R^2$ are as previously defined.

In this application:

"thermodynamically-favored" means the reaction product that has the greatest stability, or has the least free energy, of the possible products of the reaction;

"kinetically-favored" means the reaction product that is formed more quickly than the other possible products of the reaction;

"polymer" or "polymeric" means a molecule having two or more repeating units;

"polythiol" means a molecule having two or more thiol functionalities;

"polyol" means a molecule having two or more alcohol functionalities;

"polyamine" means a molecule having two or more amino functionalities; and

"polymaleamic acid" means a molecule having two or more maleamic acid functionalities.

The present invention method provides a high yield, preferably greater than 80 percent theoretical yield, of isomaleimides using inexpensive reagents and catalysts. Isomaleimides, especially polyisomaleimides, that are liquids at working temperatures allow ease of handling and essentially 100% solids processing, avoiding an adverse environmental impact. The polymers of the present invention, which can be obtained in 100% solids reactions, also have the advantage of reduced cost of manufacture and isolation, reduced adverse environmental impact, as well as ease of handling and ease of application in product form.

In a preferred embodiment, the present invention provides polymaleamides having physical properties equivalent or superior to polyurethanes but, in contrast to polyurethanes, are not prepared from potentially hazardous precursors (e.g., isocyanate-functional monomers). The present invention polymers are obtained by reacting polyisomaleimides with polyfunctional nucleophiles at moderate (ambient) temperatures. In the case where the nucleophiles are polyamines (e.g., diamines, triamines, etc.), or polythiols, the reaction may proceed in the absence of a catalyst. The polymers exhibit properties equivalent to polyurethanes, yet the monomers do not pose the hazards inherent in many isocyanates.

DETAILED DESCRIPTION OF PREFERRED EMBODIMENTS

Preparation of Isomaleimides

Synthetic routes to isomaleimides involve the cyclic dehydration of maleamic acids, wherein the kinetically-favored isomaleimide is isolated in preference to the thermodynamically-favored maleimide. Care must be taken whenever any isomaleimide is present to avoid conditions that will favor or promote the facile isomerization from desired isomaleimide to undesired maleimide. Reaction conditions to be avoided include excess acid, excess base, and reaction temperatures above about 5° C. This invention describes a novel method of preparing isomaleimides that avoids these conditions and is applicable to the preparation of both low molecular weight and high molecular weight isomaleimides, and preferably certain higher homologs, such as bis(isomaleimides) and tris(isomaleimides), in reproducible high yield and high purity. It has been found that, once they are free of catalysts that will effect isomerization, such as acids and bases, isomaleimides of the invention can be purified by such common methods as recrystallization and vacuum distillation without isomerization to the corresponding maleimides.

Previous preparatory methods for isomaleimides proceeded by the sequence of (1) reaction of maleic anhydride with a primary amine, such as n-butyl amine, to form a maleamic acid, such as N-n-butyl maleamic acid; (2) quaternization of the maleamic acid with a tertiary amine, such as triethyl amine, to form, e.g., the triethylammonium salt of N-n-butyl maleamic acid; (3) cyclic dehydration of the ammonium salt to form the desired isomaleimide, the dehydration being effected by an acid halide such as ethyl chloroformate; and (4) isolation of the isomaleimide. Alternatively, N,N'-dicyclohexylcarbodiimide (DCCD) was reacted with the maleamic acid to effect cyclic dehydration. However, DCCD is an expensive reagent, and its use on a commercial scale is not practical. Acid halides such as ethyl chloroformate are relatively inexpensive, but syntheses reported heretofore using this dehydrating agent have shown disappointingly low yields of pure isomaleimides.

The method claimed herein takes advantage of the economies offered by ethyl chloroformate while producing pure isomaleimides in reproducibly high yield. It has been discovered that, by reversing the order of addition of the acid halide dehydrating agent and the quarternizing amine, catalytic acid or basic species are not present in sufficient amount to effect isomerization of the isomaleimide, once it is formed. Additionally, deleterious side reactions are minimized. The reaction temperature preferably is maintained between about −8° to about +5° C. in the present method.

The method of the present invention provides a significant improvement in yield of isomaleimide, preferably bisisomaleimide, over previously-reported methods that do not involve the use of dicyclohexylcarbodiimide. Typically, the prior art reported yields are 50% or less of reaction products having broad distillation ranges or melting points, indicating the presence of some impurities. In contrast, by controlling both the order of addition of reactants and the rate of addition of the tertiary amine in step (b) of the method described above, thus controlling the temperature of the reaction medium, the method of the present invention routinely provides yields of greater than 85% of theoretical, and frequently provides quantitative yields. In addition, when polyisomaleimides are obtained in this manner, they are pure enough to carry forward directly into a polymerization step Thus, the present invention provides a method of preparing isomaleimides and polyisomaleimides according to the sequence:

(a) admixing at least one of a maleamic acid and a polymeric polymaleamic acid with an acid halide,
(b) reacting the admixture with a tertiary amine at a temperature sufficiently low to suppress the formation of a maleimide, and
(c) isolating the isomaleimide or polymeric polyisomaleimide.

This reaction and polymerization of the resulting polyisomaleimide with a polyamine is shown in the Reaction Sequences I and II, below. It is to be understood that other polyfunctional nucleophiles, such as a polythiol or a polyol can be substituted for a polyamine. Reaction Sequence III depicts the synthesis of a preferred bis(isomaleimide) of the invention.

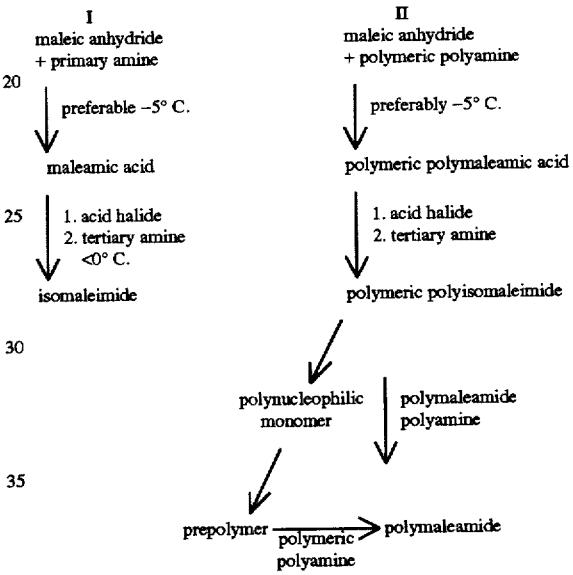

Reaction Sequence III (a preferred embodiment)

Synthesis of a Bis(isomaleimide)

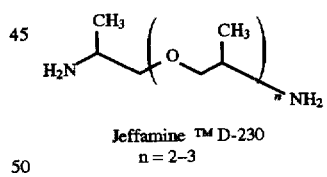

Jeffamine ™ D-230
n = 2–3

-continued
Reaction Sequence III (a preferred embodiment)

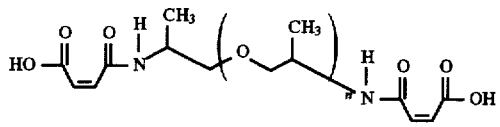

Bis(maleamic acid) from Jeffamine ™ D-230

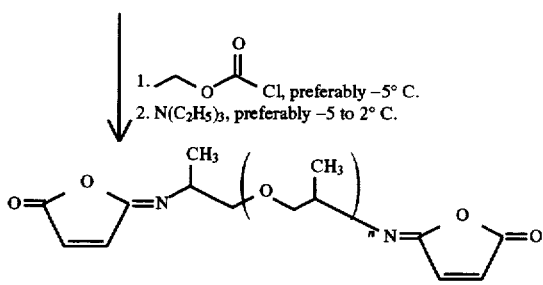

Liquid, MW = 390
PPO-Bis(isomaleimide) from Jeffamine ™ D-230
PPO = poly(propylene oxide)
n is as previously defined The reaction of maleic anhydride with a low molecular weight primary amine to form the maleamic acid reactant is well-known. Amines suitable for the reaction can be any amine having at least one primary amine (i.e., —$NH_2$) group. Any aliphatic, alicyclic, or aromatic primary amine of the formula $R^4NH_2$ is suitable for the reaction, wherein $R^4$ represents a monovalent aliphatic or alicyclic hydrocarbon radical, or a monovalent aromatic radical preferably having up to 100 carbon atoms. Representative useful primary mono-amines include methylamine, ethylamine, n-propylamine, isopropylamine, n-butylamine, isobutylamine, sec-butylamine, t-butylamine, any of the various primary pentyl, hexyl, heptyl and/or octyl amines, n-dodecylamine, cyclohexylamine, various substituted mono-amines, such as 2-chloroethylamine, chlorocyclohexylamine, methoxymethylamine, benzylamine, 2-phenylethylamine, etc., or combinations thereof.

Aliphatic and alicyclic hydrocarbons bearing more than one primary amine are also useful in the reaction, including 1,2-ethanediamine, 1,2-propanediamine, 1,3-propanediamine, 1,4-butanediamine, 1,6-hexanediamine, 1,2-, 1,3-, and 1,4-cyclohexanediamine, and bis(4-aminocyclohexyl)methane (PACM™ 20, available from Air Products and Chemicals Co., Allentown, Pa.).

Aromatic primary amines are also useful in the reaction, examples of which include aniline and naphthylamine. Aromatic primary amines bearing other substituents on the aromatic ring preferably are those in which the other substitutents are electron-donating or are only mildly electron-withdrawing. Examples of useful substituted aromatic primary amines include o-, m-, and p-toluidine, o-, m-, and p-alkoxyanilines (e.g., p-methoxyaniline), o-, m-, and p-alkylthioanilines (e.g., p-(S-methylthio)aniline, 1,2-, 1,3- and 1,4-phenylenediamine, and 4,4'-diaminodiphenylmethane. Less preferred (ie., electron-withdrawing) substituents include nitro, sulfate, sulfonate, sulfonamido, and halogen.

Polymeric primary amines preferred for use in the amination reaction include the Jeffamine™ series of amine-terminated polyethers, such as Jeffamine™ D-230, T-5000, EDR-148, D-2000 and T-403, commercially available from Huntsman Chemical Company, Salt Lake City, Utah and amine-terminated poly(tetramethyleneoxides) (PMO) such as bis(3-aminopropyl)polytetrahydrofuran (poly TBF) 350, -750, -1100, and -2100, commercially available from BASF Corporation, Mount Olive, N.J. Amine-terminated poly (dimethylsiloxanes), as described in U.S. Pat. Nos. 5,214, 119 and 5,290,615, incorporated by reference herein, are also useful in the method of the present invention.

Bis(isomaleimides) prepared from some of the aforementioned materials include:

PTMO-bis(isomaleimide) from bis (3-aminopropyl)poly(THF) 750

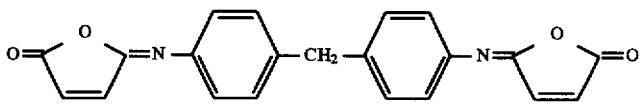

bis(isomaleimide) from 4,4'-methylene dianiline

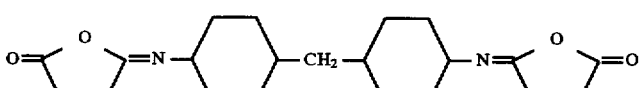

bis(isomaleimide) from PACM-20

-continued

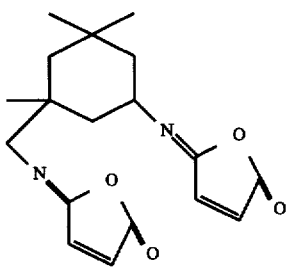

bis(isomaleimide) from isophorone diamine

Substituted maleic anhydrides may also be useful in the method of the invention. For example, substitution of phthalic anhydride for maleic anhydride would lead to isophthalimide or a polyisophthalimide, and the use of 3-methyl- or 3,4-dimethyl maleic anhydride would lead to the corresponding methyl- or dimethyl-isomaleimides. The method of the invention can be compatible with the presence of one or two substituents, e.g., methyl, chloro, phenyl, on the maleic anhydride double bond.

Maleamic acids useful in the present invention have the general formula (2)

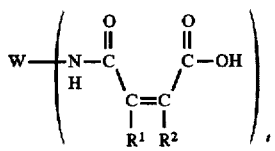

wherein W, $R^1$, and $R^2$ are as defined above, and t is an integer having a value of 1 or greater, preferably in the range of 1 to about 1,000, more preferably in the range of 1 to about 100, and most preferably 1 to about 10.

Preparation of maleamic acids is preferably carried out in an organic solvent. Solvents useful in the preparation include those in which both the maleic anhydride and the primary amine are soluble, e.g., chloroform, dichloromethane, toluene, 1,2-dichloroethane, tetrahydrofuran, dioxane, methyl t-butyl ether, methyl isobutyl ketone, diethyl ether, N,N-dimethylacetamide, o-xylene, N,N-dimethylformamide, N-methylpyrrolidone, dimethyl sulfoxide, and the like. Preferably, the solvent is also immiscible with water, e.g., chloroform, toluene, 1,2-dichloroethane, methyl t-butyl ether, methyl isobutyl ketone, diethyl ether, o-xylene, and dichloromethane, because subsequent preparative steps preferably include isolation from the organic solvent after water washing.

In the prior art, the cyclic dehydration of maleamic acids or maleamide ammonium salts has been accomplished by a number of reagents: dicyclohexylcarbodiimide, trifluoroacetic anhydride, chloroacetic anhydride, ketene, and acid halides of the type represented by ethyl chloroformate. Dicyclohexylcarbodiimide, while a useful reagent, is very expensive and not suited to commercial-scale operations of this type. A byproduct of the reaction, dicyclohexylurea, must be separated from the desired product and then disposed of responsibly, both of which add cost to the process. Any of the anhydrides present difficulties in that they produce an organic acid in the course of the dehydration step, thus presenting a potential catalyst for isomerization of the desired isomaleimide to the undesired maleimide. It is to be appreciated that either the isomaleimide yield is decreased or a second mole of tertiary amine (see below) desirably is used to neutralize the acid. Again, byproducts, such as trifluoroacetic acid ammonium salts, must be separated and disposed of. This adds to the expense of the reaction. Ketene generation on an industrial scale requires considerable capital expense, and the unstable ketene must be used immediately.

These difficulties in the prior art method have now been overcome. In the present invention, ethyl chloroformate represents a useful and preferred alternative to the above methods. It is inexpensive, and the byproducts from its reaction are ethyl alcohol and carbon dioxide.

In general, acid halides useful in the cyclic dehydration step of the present method are encompassed by compounds of formula (3):

$$R^3-O-C=O \overset{X}{|} \quad (3)$$

wherein $R^3$ represents a monovalent aliphatic, alicyclic, or aromatic radical having at least one, preferably 2 to 12, carbon atoms; preferably $R^3$ is a hydrocarbon radical; and X represents a chlorine, bromine, fluorine or iodine atom. Illustrative examples of $R^3$ include methyl, ethyl, n-propyl, n-butyl, n-amyl, n-hexyl, 2-ethyl-n-hexyl, n-heptyl, n-octyl, n-nonyl, n-dodecyl, and cyclohexyl. A particularly useful embodiment is ethyl chloroformate, wherein $R^3$ is $C_2H_4$, and X is chlorine.

Any of the organic tertiary amines can be reacted with maleamic acid to prepare the corresponding ammonium salt. Particularly preferred is an organic tertiary amine free of interfering groups such as —COOH (carboxylic acid) and —$NH_2$ (amino), as well as olefinic or acetylenic groups. Organic tertiary amines useful in the method of the invention include trimethylamine, triethylamine, tri-n-propylamine, tri-n-butylamine, tri-n-amylamine, tri-n-hexylamine, tri-(2-ethyl-n-hexyl)amine, tri-n-heptylamine, dimethyl butylamine, methyl hexyl propylamine, N-methyl-N-ethylaniline, N,N'-dimethyl-p-methoxyaniline, N-methylmorpholine, N-ethylmorpholine, N,N'-dimethylanisidine, 2-chloropyridine, 4-chloropyridine, quinuclidine, quinoline, 1,4-diazabicyclo[2.2.2]octane, N,N'-dimethylpiperazine, and the like, and combinations thereof. Preferably, the organic tertiary amine will be a liquid at ambient conditions (20°–23° C. at atmospheric pressure), for ease of handling and mixing. Most preferably, the organic tertiary amine is triethylamine, for reasons of cost, availability, and ease of handling.

In a preferred embodiment, isomaleimides of the invention are prepared as follows: a solution of maleic anhydride in an appropriate solvent, such as dichloromethane, is treated at a temperature of approximately –5° C. with a stoichiometric amount of a primary amine. The maleamic acid thus obtained is treated with an equimolar amount of ethyl chloroformate all at once while maintaining the reaction mixture at −5° C. Then, a solution of triethylamine in dichloromethane is added dropwise to the stirred mixture at such a rate as to maintain the reaction temperature below 0° C. On completion of the triethylamine addition, a considerable amount of white triethylamine hydrochloride precipitate is seen. The reaction mixture is allowed to warm to room temperature with stirring, during which $CO_2$ outgassing is observed. The amine salt is separated by filtration and the remaining dichloromethane solution is washed with saturated $NaHCO_3$ solution and distilled water. The dichloromethane layer is separated and dried, and the solvent is removed. The isomaleimide thus obtained can be used as is or can be further purified by, e.g., distillation, column chromatography, or recrystallization.

Polymaleamides

Reaction of novel polymeric liquid polyisomaleimides of the invention with organic polyamines comprising two or more primary amine groups, two or more secondary amine groups, or at least one primary and at least one secondary amine groups, polynucleophilic nonphenolic polyols or polynucleophilic polythiols, has now been successfully demonstrated in the absence of a solvent. It is particularly significant that, in the case where nucleophiles are polyamines or polythiols, this reaction can take place without a catalyst at approximately 20°–23° C. The resulting polymers exhibit useful physical and chemical properties. For example, polymaleamides prepared according to the invention exhibit significantly greater heat resistance, i.e., higher decomposition temperatures, as measured by Thermogravimetric Analysis, than analogous polyurethanes. Data shown in Tables 1 and 2 indicate decomposition temperatures in excess of 310° C., with many examples as high as 375° C., as compared with typical decomposition temperatures of polyurethanes of about 300° C.

Organic polyamines suitable as monomers that react with polyisomaleimides include any of a number of commercially-available polymeric polyamines. Examples include the Jeffamine™ series of amine-terminated polyethers, such as Jeffamine D-230, T-5000, D-2000 and T-403, and the Jeffamine™ DU series of amine-terminated urea polyethers, commercially available from Huntsman Chemical Company, Salt Lake City, Utah, amine-terminated poly(tetramethyleneoxides) such as bis(3-aminopropyl) polytetrahydrofuran 350, -750, -1100, and -2100, commercially available from BASF Corporation, Mount Olive, N.J., the Hycar™ series of amine-terminated butadiene-acrylonitrile (ATBN) copolymers such as Hycar™ 1300X21 and 1300X16, commercially available from B. F. Goodrich Co., Cleveland, Ohio and the Versalink™ series of amine-terminated polytetrahydrofurans and polypropylene oxides, commercially available from Air Products and Chemicals, Inc., Allentown, Pa. Amine-terminated poly (dimethylsiloxanes), as described in U.S. Pat. Nos. 5,214,119 and 5,290,615, incorporated by reference herein, are also useful in the method of the present invention. In addition, oligomeric alkyleneamines such as $H_2N$—$(CH_2)_m$—NH—$(CH_2)_m$—$NH_2$, wherein m=5–100 may be used.

A second group of monomer species is represented by thiols having two or more reactive —SH groups. When polymerized with polymeric polyisomaleimides, the thiols may be non-polymeric compounds such as ethylene bis(3-mercaptopropionate), trimethylolpropane tris(3-mercaptopropionate) and pentaerythritol tetra-(3-mercaptoproprionate), all of which are commercially available from Evans Chemetics, Lexington, Mass. The thiol monomers may also be polymeric, as represented by Capcure™ 3-800, a thiol end-capped polymer commercially available from Henkel Corporation, LaGrange, Ill. Polymeric bis-thiol curing agents known in the epoxy resin art may also be used as monomers with polyisomaleimides, including, for example, thiol-terminated polysulfide polymers such as LP-2™, LP-3™, LP-12™, and the like that are commercially available from Morton International, Inc., Chicago, Ill. All of the polymers comprising the reaction product of polyfunctional thiols or polyfunctional thiol-containing copolymers with isomaleimides are believed to be novel.

A third group of monomer species is represented by certain organic polyhydroxy compounds (i.e., nonphenolic polyols) comprising two or more —OH groups per molecule. When polymerized with polymeric polyisomaleimides, polyols may be non-polymeric aliphatic, cycloaliphatic or alkanol-substituted arene polyols (preferably free of dihydric or polyhydric phenols to improve flexibility in the polymer) or mixtures thereof, having up to 18 carbon atoms and two to five, preferably two to four, hydroxy groups. "Dihydric or polyhydric phenols" means compounds having 2 or more —OH groups bound directly to aromatic ring carbon atoms.

Examples of useful polyols include 1,2-ethanediol, 1,2-propanediol, 1,2-propanediol, 1,4-butanediol, 1,3-butanediol, 2-methyl-1,3-propanediol, 2,2-dimethyl-1,3-propanediol, 2-ethyl-1,6-hexanediol, 1,5-pentanediol, 1,6-hexanediol, 1,8-octanediol, glycerol, trimethylolpropane, pentaerythritol, quinitol, mannitol, sorbitol, diethylene glycol, triethylene glycol, tetraethylene glycol, 2-ethyl-2-(hydroxymethyl)-1,3-propanediol, 2-ethyl-2-methyl-1,3-propanediol, 2-ethyl-1,3-pentanediol, 2,2-oxydiethanol, 1,4-cyclohexanedimethanol, 1,4-benzenedimethanol, and 2-butene-1,4-diol. Other examples of useful polyols are disclosed in U.S. Pat. No. 4,503,211.

Polymeric polyols include polyethylene and polypropylene oxide polymers in the molecular weight range of from about 200 to about 20,000, such as the Carbowax™ series of poly(ethylene oxide) compounds (available from Union Carbide Corp., Danbury, Conn.), and the ARCOL™ series of poly(propylene oxide) compounds (available from ARCO Chemicals, Newtown Square, Pa.), polyester polyols, such as the caprolactone polyols in the molecular weight range of from about 200 to about 5000, such as the Tone™ series of polyols (available from Union Carbide), poly (tetramethylene ether) glycols in the molecular weight range of from about 200 to about 4000, such as the Terathane™ series of polyols (available from DuPont Co., Wilmington, Del.), hydroxy-terminated polybutadiene materials, such as the Poly bd™ series of polyols (available from Elf Atochem, Philadelphia, Pa.), and random copolymers of poly (tetramethylene oxide)/polycarbonate, such as the Poly-THF™ CD series of polyols (available from BASF).

The above-noted polymeric polyamines, polyols, or polythiols may be reacted with polyisomaleimides that are non-polymeric (i.e., those polyisomaleimides prepared from the reaction of maleic anhydride and a non-polymeric primary polyamine) or with polyisomaleimides that are themselves polymers. It is preferable that the reaction mixture in either case be homogeneous, e.g., the polyamine, polyol, or polythiol (or combinations thereof) and polyisomaleimide are preferably soluble in or miscible with one another.

Polymers of polyisomaleimides and polyamines may also include certain short chain, non-polymeric polyfunctional comonomers, often referred to as "chain extenders". In a manner analogous to polyurethane systems, amines bearing two or more, preferably two, primary amine groups, secondary amine groups, or a combination of primary and secondary amine groups, or polyols bearing two or more, preferably two, hydroxyl groups, may be coreacted with polyisomaleimides and polyamines to modify the properties of the resulting polymers. Such chain extending agents may be used to increase phase separation in the polymer by introducing hard segments into the polymer matrix that also increase the tensile strength and the glass transition temperature of the polymer. Organic diamines useful as chain extending agents include aliphatic and alicyclic hydrocarbons bearing more than one primary amine, including diaminomethane, 1,2-ethanediamine, 1,2-propanediamine, 1,3-propanediamine, 1,4-butanediamine, 1,6-hexanediamine, 1,2-, 1,3-, and 1,4-cyclohexanediamine, bis(4-aminocyclohexyl)methane (PACM™ 20, available from Air Products Corporation, Allentown, Pa.), Jeffamine™ EDR-148 (diethyleneglycol diethylamine), commercially available from Hunstman Chemical Co., Salt Lake City, Utah, Ethacure™ 100(diethyltoluene diamine), commercially available from Albemarle Corp., Baton Rouge, La., Primene MD™ ((1,8-diamino-p-menthane), commercially available from Rohm & Haas Co., Philadelphia, Pa.), Curing Agent H-2™ (a mixture of ethylenediamine and methyl isobutyl ketone ketimine), commercially available from Shell Chemicals Company, Houston, Tex., and the Unilink™ series of aromatic secondary diamines, such as Unilink™ 4100, 4102, 4132, 4200, and 4230, commercially available from UOP, Des Plaines, Ill.

Additional difunctional amines useful as chain extenders include 4,4'-methylene bis(o-chloroaniline) (MOCA or MBOCA), 4,4'-methylene bis(3-chloro-2,6-diethylaniline (MCDEA), propylene glycol bis(4,4'-aminobenzoate), 3,5-di(thiomethyl)-2,4-toluene diamine, methylene bis(4,4'-aniline) (MDA), ethyl-1,2-di(2-amino thiophenol), 4-chloro-3,5-diamino isobutylbenzoate, N,N'-dialkyl (methylene dianiline), N,N-dialkyl(1,4-diaminobenzene), and combinations thereof.

Examples of useful diol chain extenders include those selected from the group consisting of 1,4-butanediol, ethylene glycol, diethylene glycol, dipropylene glycol, neopentyl glycol, 1,6-hexanediol, 1,4-cyclohexane dimethanol, bis(2-hydroxyethyl)hydroquinone (HQEE), and combinations thereof The amount of chain extender used is sufficient to achieve the desired polymer property modification.

Combinations of amine and diol chain extenders can be used.

Prepolymers comprising the reaction product of polyisomaleimides and polyfunctional monomers are also within the scope of the present invention. The preparation and use of prepolymers is well-known in polymer chemistry, wherein a stoichiometric excess of one monomer is reacted with the other to form a reaction intermediate having end groups capable of further polymerization reaction. For instance, in polyurethane chemistry, a "pure" prepolymer has a stoichiometry with an NCO/OH ratio of 2/1 or less, whereas a "quasi" prepolymer has an NCO/OH ratio greater than 2/1. In the present invention, both "pure" and "quasi" prepolymers can be prepared. For example, polyisomaleimides of the invention can be reacted in stoichiometric excess with amine-functional polymers to give isomaleimide-terminated prepolymers that can be further reacted with, e.g., the same or different amine-functional polymers, to give useful materials. In the same manner, polyisomaleimides can be reacted with polyols or polythiols to prepare prepolymers.

In the reactions below,

Y, T, A, $R^1$, $R^2$, m, and n are as previously defined, and wherein A and Y are independently selected, and p is an integer of two or more and represents the degree of polymerization of the repeating unit, which is controllable via the exact ratio of equivalence of monomers, preferably p is in the range of 2 to 50,000, more preferably 2 to 1000.

Reaction Sequence IV depicts the synthetic route for varied types of prepolymers:

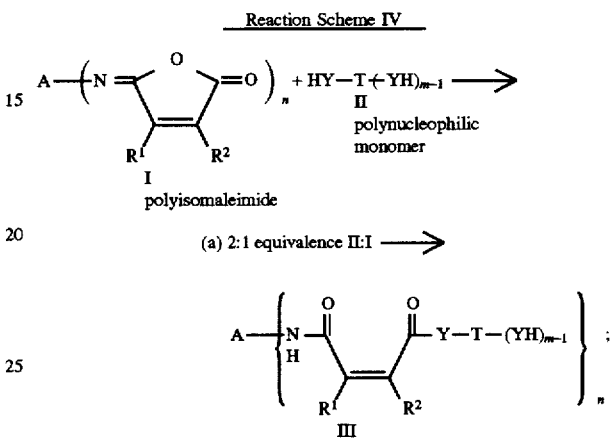

wherein the term "equivalence" means the number of moles of functional groups per each monomer.

Examples of this prepolymer structure for different values of m and n follow:

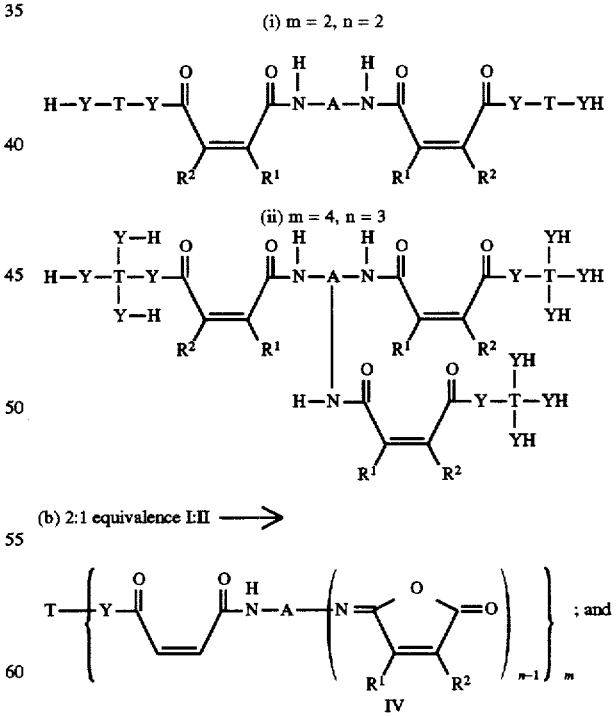

Examples of this prepolymer structure for different values of m and n are as follows:

(i) m = 2, n = 2
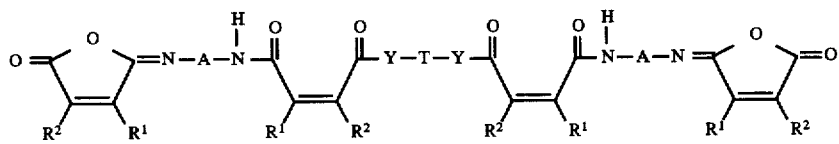
(ii) m = 4, n = 3
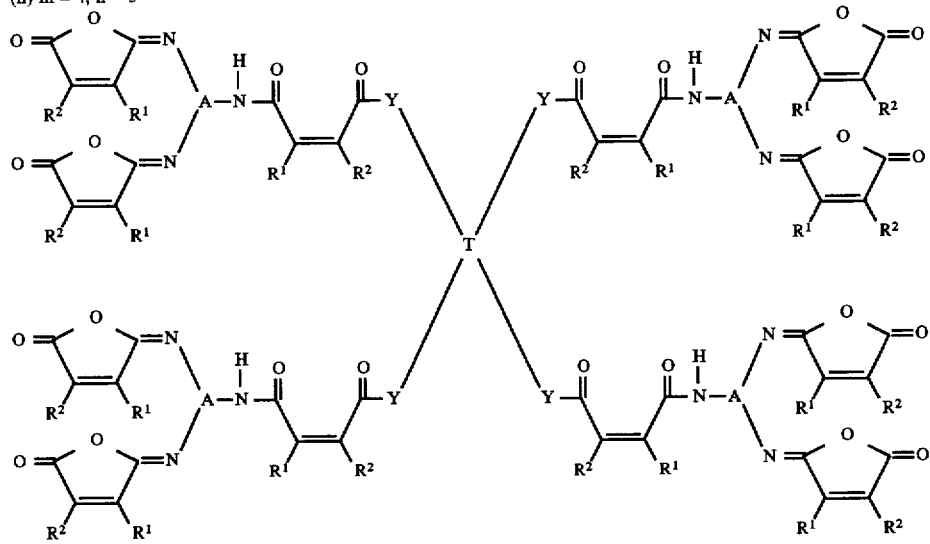
(c) much less than 2:1 equivalence of monomers ⟶ 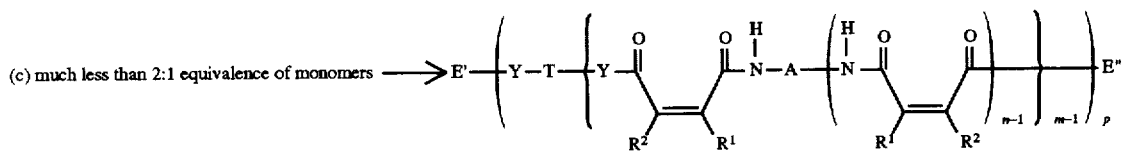
where E' can be H and E" can be —Y—T—(Y—H)$_{m-1}$
(signifying an excess of polynucleophile); or
E' can be
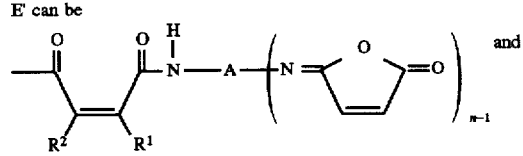
and
E" can be
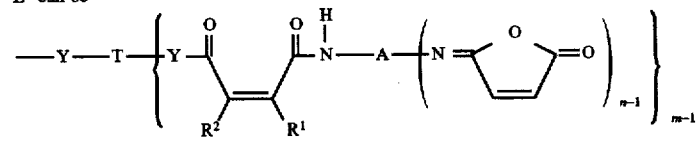
(signifying an excess of polyisomaleimide).
Examples of the prepolymer structure for different values of m and n are as follows:

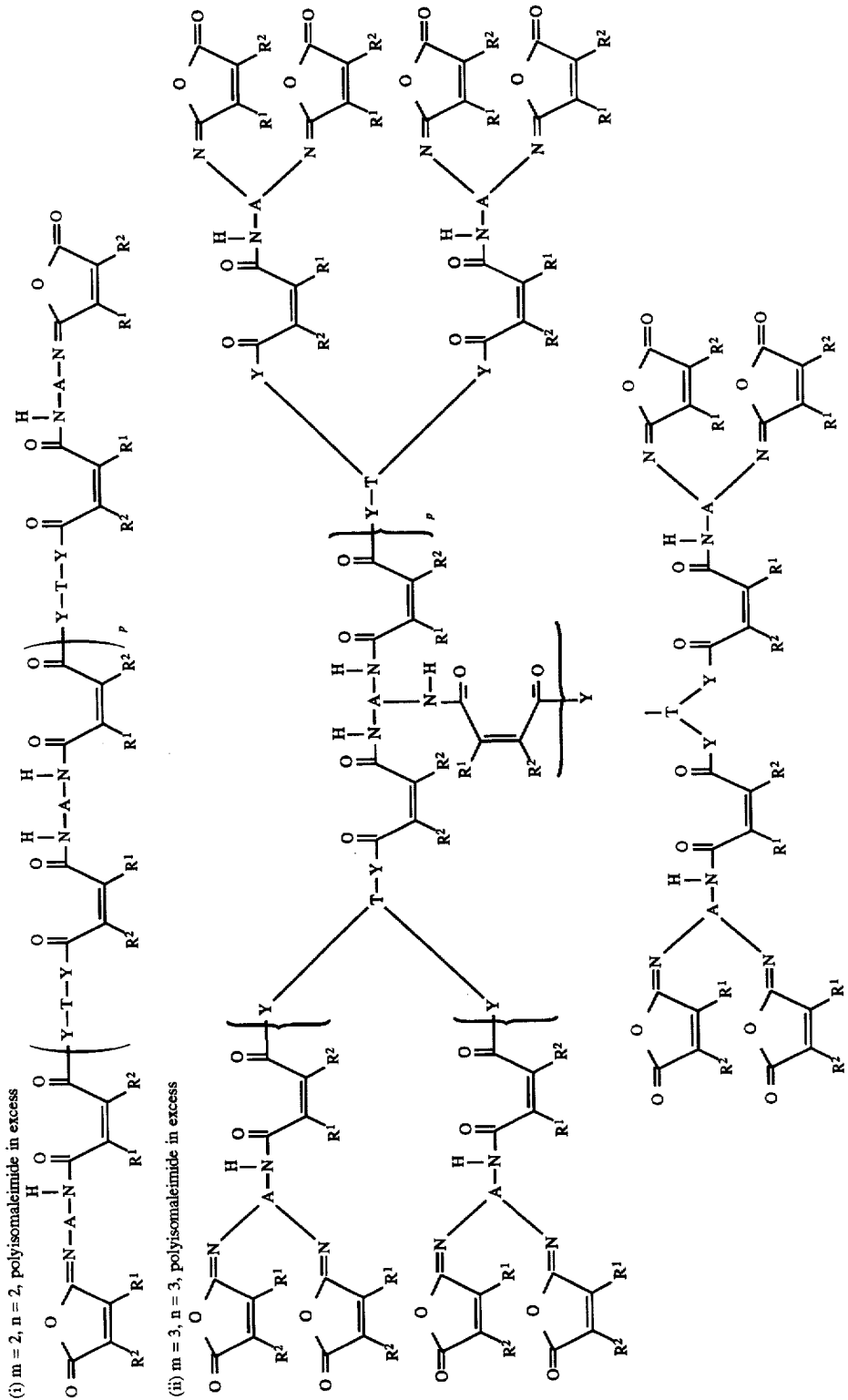

Due to the statistical nature of such reactions, the products depicted in reactions (a) and (b) above can contain minor quantities of molecules having a degree of polymerization greater than 1. Additionally, in reaction (c), products are formed which constitute a distribution of degrees of polymerization p.

Polymerization reactions of polyisomaleimides and polyamines, polyols, or polythiols may be carried out in an organic solvent or, preferably, may be carried out in the absence of any solvent (e.g., neat). When a solvent is used, the solvent preferably is one in which both monomers and the resulting polymer are soluble, such as cyclic and linear ketones, cyclic and linear alkyl ethers, halogenated alkanes, aromatic hydrocarbons, cyclic and linear alkyl esters, and the like.

Polymers of the invention find use as adhesives, sealants, molding compounds, protective coatings, binders for abrasives, potting compounds, and crosslinking agents for hybrid materials systems.

Objects and advantages of this invention are further illustrated by the following examples, but the particular materials and amounts thereof recited in these examples, as well as other conditions and details, should not be construed to unduly limit this invention.

Evaluation Methods

Tensile Strength & Percent Elongation

Tensile strength & percent elongation testing was performed on an Sintech Model 10 tensile tester (MTS Systems Corp., Eden Prairie, Minn.). Testing was performed essentially according to ASTM Method D 638-89. Dumbbell specimens were prepared of approximately 0.318 cm (0.125 inch) in width and approximately 0.159 cm (0.0625 inch) in thickness (cross-sectional area of approximately 0.05 cm$^2$) or of approximately 0.635 cm (0.250 inch) in width and approximately 0.119 cm (0.0469 inch) in thickness (cross-sectional area of approximately 0.076 cm$^2$) and were tested at a crosshead speed of 5.08 cm/min (2 inches/min) or 50.8 cm/min (20 inches/min).

Tear Resistance

Tear resistance testing was performed on a Sintech Model 10 tensile tester. Testing was performed essentially according to ASTM Method D 624-86. Samples of approximately 0.159 cm (0.0625 inch) in thickness were prepared using a Die C type die and were tested at a crosshead speed of 5.08 cm/min (2 inches/min) or 50.8 cm/min (20 inches/min).

Gel Time

Gel time determination was performed essentially according to ASTM Method D 1338-56.

Decomposition Temperature

Decomposition temperature was determined by Thermogravimetric Analysis (TGA) essentially according to ASTM method E1131-93, using a Perkin-Elmer TMA-7 analyzer (Perkin-Elmer Corp., Norwalk, Conn.). The sample was heated at 10° C./min from 25° C. to 1000° C. under a nitrogen flow of 50 mL/min.

EXAMPLE 1

Synthesis of the bis(isomaleimide) of Jeffamine™ D-230

Bis(maleamic acid): A 3-liter reaction flask (oven-dried) equipped with a mechanical stirrer, N$_2$ inlet and bubbler, addition funnel, and thermometer was charged with 99.0 g maleic anhydride and 1500 mL dichlioromethane, and the resulting slurry was stirred under a slow N$_2$ purge. An ice bath was placed around the flask and the solution was cooled to less than 10° C. A solution of 121.7 g Jeffamine™ D-230 poly(propyleneoxide) diamine (Huntsman Chemical Co., Salt Lake City, Utah), in approximately 150 mL dichloromethane was added dropwise while the temperature was maintained at less than 10° C. The solution remained homogeneous throughout the addition. The solution was allowed to stir overnight.

Bis(maleamic acid) cylodehydration to bis (isomaleimide): The bis(maleamic acid) solution thus obtained was cooled to 0° C. with an ice/salt bath, then 96.6 mL (109.6 g) ethyl chloroformate (commercially available from Aldrich Chemical Co., Milwaukee, Wis.) was added all at once. This solution was stirred briefly then treated dropwise with 140.8 mL (102.2 g) triethylamine (Aldrich) dissolved in approximately 110 mL dichloromethane. The initial rate of addition was about 60 drops/minute. During this addition, the reaction exothermed from 0° to 1° C., and outgassing from liberated CO$_2$ commenced when about one-half of the reagent had been added. The rate of addition of triethylamine solution was reduced in order to control the exotherm and keep the temperature in the range of −1° to 0° C. Towards the end of the addition, NEt$_3$●HCl (wherein Et=ethyl) began appearing as a white precipitate. The appearance of the reaction mixture at the end of the addition was an opaque orange-brown slurry consisting of the bis (isomaleimide) product in solution along with a large amount of precipitated NEt$_3$●HCl. The ice/salt bath was removed and the reaction mixture was quickly warmed to 20° C., causing considerable outgassing to occur. NEt$_3$●HCl was removed by filtration, and the filtrate was washed with saturated NaHCO$_3$ solution (1×2 liters) then distilled water (2×2 liters). The dichloromethane layer was dried over Na$_2$CO$_3$, filtered, and stripped of solvent to give the bis(isomaleimide) product as a brown oil. This was placed in a vacuum oven and heated at 60°–65° C. overnight to remove additional volatiles. Yield: 176 g (89%). NMR analysis determined the purity of this material to be greater than 94%. This material was suitable for use in formulation work without further purification.

EXAMPLE 2

Synthesis of the bis(isomaleimide) of α,ω-bis(aminopropyl) poly(tetrahydrofuran)

Bis(maleamic acid) synthesis: A 5-liter reaction flask (oven-dried) equipped with a mechanical stirrer, N$_2$ inlet and bubbler, addition funnel, and thermometer was charged with 65.05 g maleic anhydride and 1700 mL dichloromethane, and the resulting slurry was stirred under a N$_2$ purge. After most of the maleic anhydride dissolved an ice bath was used to cool the reaction to less than 10° C., then a solution of 248.76 g α,ω-bis(aminopropyl) poly(tetrahydrofuran)-750 (commercially available from BASF Corp., Mount Olive, N.J.) in approximately 150 mL dichloromethane was added dropwise. During this addition the temperature was maintained at less than 10° C. The solution remained homogeneous throughout the addition. The solution was allowed to stir overnight.

Bis(maleamic acid) cyclodehydration to bis (isomaleimide): The bis(maleamic acid) solution thus obtained was cooled to −6° C. with an ice/salt bath, then 63.4 mL (72.0 g) ethyl chloroformate was added all at once. This solution was stirred briefly then treated dropwise with a solution of 92.5 mL (67.2 g) triethylamine in approximately 100 mL dichloromethane. Rate of addition was initially about 100 drops/minute. During this addition, the reaction exothermed from −6° to 0° C.; outgassing from liberated CO$_2$ commenced when about one-fourth of the reagent had been added. The rate of addition of triethylamine solution was reduced in order to control the exotherm and keep the temperature below 2° C. Towards the end of the addition, NEt$_3$●HCl began appearing as a white precipitate. The appearance of the reaction mixture at this point was a light orange solution with a small amount of white precipitate. The ice/salt bath was removed and the reaction mixture was quickly warmed to 20° C., causing considerable outgassing to occur. The dichloromethane solution was washed with saturated NaHCO₃ solution (1×2 liters) and distilled water (2×2 liters), then dried over Na₂CO₃, filtered, and stripped of solvent to give the bis(isomaleimide) product as a brown-orange oil. The oil was heated at 60°–65° C. overnight under vacuum to remove additional volatiles. Yield: 290 g (97%). NMR analysis determined this material to be free of maleimide and to have a purity of greater than 99%. This polymer was suitable for use in materials formulation work without further purification.

EXAMPLE 3
Synthesis of the bis(isomaleimide) of 4,4'-methylenedianiline

Bis(maleamic acid) synthesis: A 3-liter reaction flask (oven-dried) equipped with a mechanical stirrer, N₂ inlet and bubbler, addition funnel, and thermometer was charged with 123.6 g maleic anhydride and 1300 mL dichloromethane and the resulting slurry was stirred under a N₂ purge. After most of the maleic anhydride dissolved an ice bath was used to cool the mixture to 1° C., then a solution of 125.0 g 4,4'-methylene dianiline (Aldrich) in approximately 600 mL dichloromethane was added dropwise. During this addition the temperature was maintained below 5° C. Soon after commencing addition of the diamine, the bis(maleamic acid) product precipitated from solution as a yellow solid. The solution was allowed to stir overnight. A large quantity of the yellow-orange bis(maleamic acid) had precipitated by the next morning.

Bis(maleamic acid) cyclodehydration to bis (isomaleimide): The bis(maleamic acid) slurry was cooled to −4° C. with an ice/salt bath, then 120.5 mL (136.8 g) ethyl chloroformate was added all at once. This slurry was stirred briefly, then a solution of 175.6 mL (127.5 g) triethylamine in 460 mL dichloromethane was added dropwise. Addition of the NEt₃ rendered soluble the bis(maleamic acid) in the dichloromethane solvent, facilitating its reaction with ethyl chloroformate and conversion to bis(isomaleimide). Simultaneously, NEt₃●HCl precipitated as a reaction by-product. During this addition, the reaction exothermed from −4° to −2° C. The rate of addition of triethylamine solution was controlled such that the reaction temperature was maintained below −2° C.; this addition was complete in 2 to 3 hours. The ice/salt bath was removed and the reaction mixture was filtered immediately and the dichloromethane filtrate was washed with saturated NaHCO₃ solution (1×2 liters) and distilled water (2×2 liters). The dichloromethane layer was dried over Na₂CO₃, filtered, and stripped of solvent to give the bis(isomaleimide) product as a yellow solid. Additional product was recovered from the filter cake by washing with water followed by vacuum-drying of the remaining solid. The combined batches represented a crude yield of 94%. This product was determined via NMR to contain about 92% of the desired bis(isomaleimide), the rest of the composition being comprised of maleimide and ester impurities. These impurities were easily removed by trituration overnight under diethyl ether, followed by filtration and vacuum drying to give a free-flowing, bright yellow powder containing greater than 99% bis(isomaleimide) by NMR. Recovery from the purification step was 91%, giving an overall yield of 86%. The purified material exhibited a sharp melting point at 155°–156° C. and was sufficiently pure for use in materials formulation work.

EXAMPLE 4
Synthesis of the bis(isomaleimide) of PACM-20

Bis(maleamic acid) synthesis: A 5-liter reaction flask (oven-dried) equipped with a mechanical stirrer, N₂ inlet and bubbler, addition funnel, and thermometer was charged with 100.42 g maleic anhydride and 1700 mL dichloromethane, and the resulting slurry was stirred under a slow N₂ purge. The solution was cooled to below 10° C. with an ice bath, then treated with a solution of 107.71 g bis(4-aminocyclohexyl)methane (PACM-20 diamine, commercially available from Air Products Corp., Allentown, Pa.) in approximately 100 mL dichloromethane, while the temperature was maintained at below 10° C. The bis(maleamic acid) precipitated as a white solid as the addition proceeded. The slurry was allowed to stir overnight.

Bis(maleamic acid) cyclodehydration to bis (isomaleimide): The bis(maleamic acid) slurry was cooled to 0° C. with an ice/salt bath, then 98 mL (111.2 g) ethyl chloroformate was added all at once. This slurry was stirred briefly then 143 mL (103.8 g) triethylamine diluted with approximately 100 mL dichloromethane was added dropwise to the reaction. Addition of the NEt₃ rendered soluble the bis(maleamic acid) in the dichloromethane solvent, facilitating its reaction with ethyl chloroformate and conversion to bis(isomaleimide). Simultaneously, NEt₃●HCl precipitated as a reaction by-product. The NEt₃ solution was added at approximately 75 drops/minute, which was effective in maintaining a temperature at 0° C. Outgassing from liberated CO₂ became vigorous when about three-fourths of the reagent had been added. The ice/salt bath was removed and the reaction mixture was quickly warmed to 20° C., causing considerable outgassing to occur. NEt₃●HCl was removed by filtration and the dichloromethane filtrate was washed with saturated NaHCO₃ solution (1×2 liters) and distilled water (2×2 liters). The dichloromethane layer was dried over Na₂CO₃, filtered, and stripped of solvent to give the bis(isomaleimide) product as a brown-red solid. Vacuum drying at room temperature for two days removed additional volatiles. Yield: 171 g (91%). NMR analysis determined the purity of this material to be greater than 98%. The bis (isomaleimide) was redissolved in dichloromethane and precipitated from n-hexane to give an off-white solid having a softening point of 124°–130° C. that was determined to be greater than 99.5% pure via NMR analysis. This purified monomer was suitable for use in materials formulation work.

EXAMPLE 5
Synthesis of sec-butylisomaleimide

Maleamic acid synthesis: A 5-liter reaction flask (oven-dried) equipped with a mechanical stirrer, N₂ inlet and bubbler, addition funnel, and thermometer was charged with 142.47 g maleic anhydride and 2000 mL dichloromethane and the resulting slurry was stirred under a slow N₂ purge. The flask was cooled to less than 10° C. by an ice bath and a solution of 113.7 g sec-butyl amine (Aldrich) in approximately 100 mL dichloromethane was added dropwise while the temperature was maintained at less than 10° C. The solution remained homogeneous throughout the reaction, turning a light yellow color. The solution was allowed to stir overnight before the next step.

Maleamic acid cyclodehydration to isomaleimide: The maleamic acid solution was cooled to −8° C. with an ice/salt bath, then 148.7 mL (168.8 g) ethyl chloroformate was added all at once. This solution was stirred briefly, then a solution of 217 mL (157.5 g) triethylamine in approximately 100 mL dichloromethane was added dropwise to the stirred reaction mixture, initially at a rate of about 100 drops/ minute. During this addition, the reaction exothermed from −8° to 2° C.; outgassing from liberated $CO_2$ commenced when about one-half of the reagent had been added. The rate of addition of triethylamine solution was then reduced to keep the temperature below 2° C. Towards the end of the addition, $NEt_3\bullet HCl$ began appearing as a white precipitate. The ice/salt bath was removed and the reaction mixture was quickly warmed to 20° C., causing considerable outgassing to occur. $NEt_3\bullet HCl$ was removed by filtration and the dichloromethane filtrate was washed with saturated $NaHCO_3$ solution (1×2 liters) and distilled water (2×2 liters), then dried over $Na_2CO_3$, filtered, and stripped of solvent to give the isomaleimide product as a light orange liquid. Vacuum drying at room temperature for 15 minutes removed additional volatiles. Yield: 239 g (100 %). NMR analysis determined the purity of this material to be approximately 98%. Further purification gave a colorless liquid via vacuum distillation at 2.4 torr and 80°–102° C.

EXAMPLE 6

An elastomeric type polymer was prepared in the following manner: 33.30 g glyceryl poly(oxypropylene) triamine (Jeffamine™ T-5000, commercially available from Huntsman Chemical Co., Salt Lake City, Utah) and 6.66 g diethyltoluenediamine (DETDA, Ethacure™ 100, commercially available from Albemarle Corp., Baton Rouge, La.) were added to a 237 mL (8 ounce) container and mixed for about 5 minutes, until homogeneous. To this mixture was added 18.00 g bis(isomaleimide) from Example 1 (hereinafter referred to as D-230 BIMI). After approximately 3 minutes of mixing under 66 cm (30 in.) Hg vacuum, a homogeneous mixture was obtained. The mixture was poured onto a plate to a thickness of about 1.5 mm (0.06 in) and allowed to cure for at least one week at 23°±2° C. and 50±2% R.H. Samples for evaluation were prepared and tensile strength, percent elongation and tear resistance were determined. Results are shown in Table 1, below.

EXAMPLE 7

A polymer was prepared according to the method of Example 6, except that the T-5000:DETDA ratio was changed. The amine mixture consisted of 42.16 g T-5000 and 4.22 g DETDA. This was combined with 13.60 g D-230 BIMI. Evaluation results for the resultant polymer are shown in Table 1, below.

EXAMPLE 8

A polymer was prepared according to the method of Example 6, except that the DETDA was replaced with a blocked diamine. The amine mixture consisted of 35.20 g T-5000 and 7.04 g ethylenediamine/methyl isobutyl ketone ketimine (EDA/MIBK) (Epon™ Curing Agent H-2, commercially available from Shell Chemical Co., Houston, Tex.). This was combined with 16.00 g D-230 BIMI. Evaluation results for the resultant polymer are shown in Table 1, below.

EXAMPLES 9–11

Polymers were prepared according to the method of Example 8, except that the T-5000:EDA/MIBK ratio was varied:

| Example | T-5000, g | EDA/MIBK, g | D-230 BIMI, g |
|---|---|---|---|
| 9 | 54.00 | 0.00 | 5.51 |
| 10 | 43.20 | 4.32 | 12.00 |
| 11 | 32.00 | 9.60 | 20.12 |

Test results for the resultant polymers are shown in Table 1, below.

EXAMPLE 12

A plastic type polymer was prepared as follows: 32.88 g of a mercaptan-terminated polymer (Capcure™ 3-800, commercially available from Henkel Corp. LaGrange, Ill.) and 24.00 g D-230 BIMI were added to an 237 mL can and mixed under 66 cm (30 in.) Hg vacuum for 1.5–3 minutes, until homogeneous. The mixture was poured into a Type IV mold (ASTM D-638) and allowed to cure for at least one week at 23±20° C and 50±2% R.H. Evaluation results for the resultant polymer are shown in Table 1, below.

EXAMPLE 13

A polymer was prepared according to the method of Example 12, except that 19.91 g glycol dimercaptopropionate (ethylene bis(3-mercaptopropionate), commercially available from Evans Chemetics, Lexington, Mass.) were combined with 33.00 g D-230 BIMI. Evaluation results for the resultant polymer are shown in Table 1, below.

EXAMPLE 14

A polymer was prepared according to the method of Example 12, except that 22.22 g trimethylolpropane tris-(3-mercaptopropionate) (Evans Chemetics) were combined with 33.00 g D-230 BIMI. Evaluation results for the resultant polymer are shown in Table 1, below.

EXAMPLE 15

A polymer was prepared according to the method of Example 12, except that 20.46 g pentaerythritol tetra-(3-mercaptopropionate) (Evans Chemetics) were combined with 33.00 g D-230 BIMI. Evaluation results for the resultant polymer are shown in Table 1, below.

EXAMPLE 16

A polymer was prepared as follows: 2.86 g of the bis-isomaleimide from Example 3 (hereinafter referred to as MDA BIMI) was dissolved in 50-100 mL tetrahydrofuran (THF) in a 237 mL jar. To this solution was added 8.35 g bis(3-aminopropyl) polytetrahydrofuran 1100 (commercially available from BASF Corp., Mount Olive, N.J.) and 0.09 g EDA/MIBK. This mixture was stirred for approximately 30 minutes and cast into an open 10 cm–21 cm mold. The THF was allowed to evaporate at ambient temperature and the resulting film allowed to cure for at least one week at 23±2° C. and 50±2% R.H. Samples for evaluation were prepared and tensile strength and percent elongation data are shown in Table 2, below.

EXAMPLE 17

A polymer was prepared according to the method of Example 16, in which 3.48 g MDA BIMI dissolved in THF was combined with 2.5 g Jeffamine™ T-3000, 2.5 g Jeffamine™ D-2000 and 1.30 grams of DETDA. Samples for evaluation were prepared and tensile strength and percent elongation were determined, as shown in Table 2, below.

EXAMPLE 18

A polymer was prepared according to the method of Example 16, in which 16.86 g MDA BIMI dissolved in approximately 250–300 mL of a 1:1 solution of toluene:methyl ethyl ketone at 50° C. was combined with 45.00 g Jeffamine™ T-5000 and 5.00 g 2,2'-(ethylenedioxy)bis(ethylamine) (Jeffamine™ EDR-148). Samples for evaluation were prepared and tensile strength and percent elongation were determined, as shown in Table 2, below.

EXAMPLE 19

A polymer was prepared according to the method of Example 16, in which 3.58 g of a bis(isomaleimide) prepared from isophorone diamine (IPDA, Aldrich) according to the method of Example 3 (hereinafter referred to as IPDA BIMI) was dissolved in approximately 100 mL methylene chloride and combined with 11.34 g bis(3-aminopropyl) polytetrahydrofuran 1100 and 0.12 g EDA/MIBK. Samples for evaluation were prepared and tensile strength and percent elongation were determined, as shown in Table 2, below.

EXAMPLE 20

A polymer was prepared according to the method of Example 16, in which 5.42 g of the bis(isomaleimide) of Example 4 (hereinafter referred to as PACM BIMI) was dissolved in approximately 100 mL methylene chloride and combined with 14.42 g poly(oxypropylenediamine) (TE-220, Huntsman Chemical Co., Salt Lake City, Utah) and 2.27 g Jeffamine™ T-403. Samples for evaluation were prepared and tensile strength and percent elongation were determined, as shown in Table 2, below.

EXAMPLE 21

A polymer was prepared according to the method of Example 16, in which 10.00 g of a bis(isomaleimide) prepared from bis(3-aminopropyl) polytetrahydrofuran 350 (3ASF Corp., Mount Olive, N.J.) according to the method of Example 2, was dissolved in approximately 50 ml of methylene chloride and combined with 6.90 g bis(3-aminopropyl) polytetrahydrofuran 350. Samples for evaluation were prepared and tensile strength and percent elongation were determined, as shown in Table 2, below.

EXAMPLE 22

A polymer was prepared as follows: A solution of 1.4 g of MDA BIMI in 50 g of methylene chloride was mixed with a solution of 8.6 g Hycar™ ATBN 1300X21 (an amine-terminated butadiene-acrylonitrile copolymer, commercially available from B. F. Goodrich Co., Cleveland, Ohio) in 70 g methylene chloride for 4–5 minutes, and the resulting solution was cast into an open 10 cm×21 cm (4 inches×6 inches) mold and the solvent was allowed to evaporate at ambient temperature. The resulting polymer was allowed to cure for at least 7 days at 23±2° C. and 50±2% relative humidity. Samples for evaluation were prepared and tensile strength, percent elongation and tear resistance were determined, as shown in Table 2, below.

EXAMPLE 23

A polymer was prepared according to the method of Example 22, in which 1.60 g MDA BIMI dissolved in 50 g of methylene chloride were combined with 8.52 g Hycar™ ATBN 1300X16 in 70 g methylene chloride. Samples for evaluation were prepared and tensile strength, percent elongation and tear resistance were determined, as shown in Table 2, below.

EXAMPLE 24

A polymer was prepared according to the method of Example 22, in which 1.60 g PACM BIMI dissolved in 50 g of methylene chloride were combined with 8.24 g of Hycar™ ATBN 1300X16 in 70 g methylene chloride. Samples for evaluation were prepared and tensile strength, percent elongation and tear resistance were determined, as shown in Table 2, below.

TABLE 1

100% Solids (Solvent Free) Systems

| Example | Tensile PSI (MPa) | % Elongation | Tear PLI (KN/M) | Gel Time (min.) | Decomp. Temp, °C. |
|---|---|---|---|---|---|
| 6 | 715 (4.93) | 967 | 199 (34.8) | >120 | 375 |
| 7 | 704 (4.85) | 1,183 | 98 (17.2) | >120 | 375 |
| 8 | 951 (6.56) | 617 | 110 (19.3) | 25 | 375 |
| 9 | 95 (0.65) | 223 | 15 (2.6) | 12 | 370 |
| 10 | 395 (2.72) | 477 | 56 (9.8) | 25 | 370 |
| 11 | 295 (2.03) | 533 | 70 (12.3) | 30 | 375 |
| 12 | 1,154 (7.95) | 80 | — | <10 | 330 |
| 13 | 2,066 (14.24) | 112 | — | 3 | 310 |
| 14 | 8,735 (60.21) | 15 | — | >40 | 335 |
| 15 | 9,782 (67.42) | 15 | — | 30 | 335 |

—means not measured.

TABLE 2

Solvent Borne Systems

| Example | Tensile PSI (MPa) | % Elongation | Tear PLI (KN/M) | Decomp. Temp., °C. |
|---|---|---|---|---|
| 16 | 3,586 (24.72) | 520 | — | 400 |
| 17 | 2,217 (15.28) | 212 | — | — |
| 18 | 1,292 (89.05) | 950 | — | — |
| 19 | 2,196 (15.14) | 725 | — | — |
| 20 | 920 (6.34) | 425 | — | — |
| 21 | 712 (4.91) | 392 | — | — |
| 22 | 2,652 (18.28) | 775 | 303 (53.0) | — |
| 23 | 2,565 (17.68) | 750 | 330 (57.8) | — |
| 24 | 2,488 (17.15) | 665 | — | — |

—means not measured.

EXAMPLE 25

Isomaleimide-terminated prepolymers were prepared by stirring 5 g of α,ω-bis(isomaleimidopropyl) polytetrahydrofuran, prepared according to Example 2, amounts of Jeffamine D-2000 (an amine-terminated polyether, Huntsman Chemical Co., Salt Lake City, Utah) under a nitrogen purge he resultant prepolymers had isomaleimide/amine ratios of 2/1, 3/1 prepolymers remained liquid and had viscosities of 74,670 cps, 26,330 cps, respectively.

EXAMPLE 26

Two solutions were prepared by dissolving 25 g of 4,4'-methylenebis((2,6-diethyl phenyl)isomaleimide), prepared according to Example 3, in 100 mL tetrahydrofuran and adding 53.6 g and 26.7 g, respectively, of Jeffamine D-2000 to make prepolymers with isomaleimide/amine ratios of 2/1 and 4/1, respectively. The solutions were stirred at 23° C. for one hour, after which solvent was removed on a rotoevaporator to give a liquid prepolymer. NMR spectra confirmed the formation of a prepolymer by showing the presence of both isomaleimide and maleamide functionalities. Ten grams of the 2/1 isomaleimide/amine prepolymer was further reacted with 0.5 g of 2,2'-(ethylenedioxy)bis (ethylamine) (EDR-148) to give an elastomeric material. Ten grams of the 4/1 isomaleimide/amine prepolymer was also reacted with EDR-148 (1.14 g) to give a tough rubbery polymaleamide.

EXAMPLE 27

An elastomeric type polymer was prepared as follows: 5 grams of 1,000 MW polytetramethylene ether glycol (PolyTEF 1000, BASF Corp.) was placed in a small vial and heated to 70° C. To this was added 1.87 grams of PACM-BIMI (prepared as in Example 4). The head space of the vial was purged with nitrogen and the mixture was heated to 70° C. The PACM BIMI dissolved in the PolyTHF over a period of four hours with occasional shaking of the vial. The mixture gelled within 24 hours at 70° C. to form a clear, amber colored elastomer comprising a poly(half-ester half-maleamide).

Various modifications and alterations of this invention will become apparent to those skilled in the art without departing from the scope and spirit of this invention, and it should be understood that this invention is not to be unduly limited to the illustrative embodiments set forth herein.

We claim:

1. A method for preparing an isomaleimide or polyisomaleimide comprising the steps in sequence:

(a) admixing at least one of a maleamic acid and a polymaleamic acid with an acid halide,
    (b) reacting the admixture with a tertiary amine at a temperature sufficiently low to suppress the formation of a maleimide, and
    (c) isolating the resulting isomaleimide or polyisomaleimide.

2. The method according to claim 1 wherein said polyisomaleimide has the formula

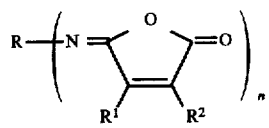

wherein R represents a polyvalent organic group derived from a polymeric primary polyamine by replacement of both hydrogen atoms from each amino group for each isomaleimide group formed, and $R^1$ and $R^2$ are the same or different and are independently selected from the group consisting of hydrogen, $C_1$ to $C_{20}$ linear, branched or cyclic aliphatic groups, $C_6$ to $C_{20}$ aromatic groups, fluorine, chlorine, bromine, and iodine, or $R^1$ and $R^2$ can be joined together to form a cyclic ring that is aromatic or alicyclic;

n represents the degree of isomaleimide functionality, and is an integer of at least 2.

3. The method according to claim 2 wherein n is an integer in the range of 2 to 50,000.

4. The method according to claim 1 further comprising the step of polymerizing said polyisomaleimide with a polynucleophilic monomer selected from the group consisting of polythiols, nonphenolic polyols, and primary or secondary polyamines, and combinations thereof in the absence of solvent.

5. The method according to claim 1 wherein said acid halide has the formula

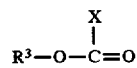

wherein $R^3$ represents a monovalent aliphatic, alicyclic, or aromatic hydrocarbon radical having one or more carbon atoms; and X represents chlorine, bromine, fluorine or iodine.

6. The method according to claim 5 wherein $R^3$ is selected from the group consisting of methyl, ethyl, n-propyl, n-butyl, n-amyl, n-hexyl, 2-ethyl-n-hexyl, n-heptyl, n-octyl, n-nonyl, n-dodecyl, and cyclohexyl groups.

7. The method according to claim 5 wherein said acid halide is ethyl chloroformate.

8. The method according to claim 1 wherein said maleamic acid has the formula

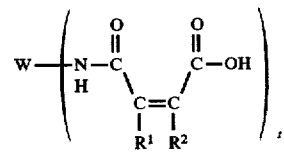

wherein

W is a polyvalent organic group which can include 0 to 100 heteroatoms that interrupt carbon chains and optionally substituent groups, provided that W and its substituent groups do not interfere with formation of isomaleimides, polyisomaleimides, and polymers of the invention, $R^1$ and $R^2$ are the same or different and are independently selected from the group consisting of hydrogen, $C_1$ to $C_{20}$ linear, branched or cyclic aliphatic groups, $C_6$ to $C_{20}$ aromatic groups, fluorine, chlorine, bromine, and iodine, or $R^1$ and $R^2$ can be joined together to form a cyclic ring that is aromatic or alicyclic;

and t is an integer having a value greater than 1.

9. The method according to claim 1 wherein said tertiary amine is an aliphatic or aromatic tertiary amine which is free of carboxylic acid, amino, olefinic, and acetylinic groups.

10. The method according to claim 9 wherein said tertiary amine is selected from the group consisting of trimethylamine, triethylamine, tri-n-propylamine, tri-n-butylamine, tri-n-amylamine, tri-n-hexylamine, tri-(2-ethyl-n-hexyl)amine, tri-n-heptylamine, dimethyl butylamine, methyl hexyl propylamine, N-methyl-N-ethylaniline, N,N'-dimethyl-p-methoxyaniline, N-methylmorpholine, N-ethylmorpholine, N,N'-dimethylanisidine, 2-chloropyridine, 4-chloropyridine, quinuclidine, quinoline, and N,N'-dimethylpiperazine, and combinations thereof.

11. The method according to claim 9 wherein said tertiary amine is triethylamine.

12. The method according to claim 4 wherein said polynucleophilic monomer is a polyamine comprising two or more amine groups selected from the group consisting of primary and secondary amines.

13. The method according to claim 12 wherein said polyamine is selected from the group consisting of amine-terminated polyethers, amine-terminated butadiene-acrylonitrile copolymers, amine-terminated poly(dimethylsiloxanes), and oligomeric alkyleneamines.

14. The method according to claim 4 wherein said polynucleophilic monomer is selected from the group consisting of polythiols and nonphenolic polyols.

15. The method according to claim 1 wherein said isomaleimide has a weight average molecular weight of greater than about 400.

16. The method according to claim 1 wherein said polyisomaleimide has a weight average molecular weight in the range of 300 to 50,000.

17. An isomaleimide comprising the formula

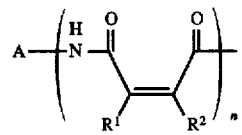

wherein R' represents an organic group derived from a polymeric primary amine by replacement of both hydrogen atoms from the amino group for the isomaleimide group formed, and $R^1$ and $R^2$ are the same or different and are independently selected from the group consisting of hydrogen, $C_1$ to $C_{20}$ linear, branched or cyclic aliphatic groups, $C_6$ to $C_{20}$ aromatic groups, fluorine, chlorine, bromine, and iodine, or $R^1$ and $R^2$ can be joined together to form a cyclic ring that is aromatic or alicyclic.

18. A polyisomaleimide comprising the formula

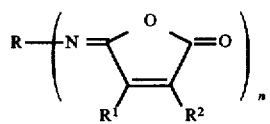

wherein R represents a polyvalent organic group derived from a polymeric primary polyamine by replacement of both hydrogen atoms from each amino group for each isomaleimide group formed, $R^1$ and $R^2$ are the same or different and are independently selected from the group consisting of hydrogen, $C_1$ to $C_{20}$ linear, branched or cyclic aliphatic groups, $C_6$ to $C_{20}$ aromatic groups, fluorine, chlorine, bromine, and iodine, or $R^1$ and $R^2$ can be joined together to form a cyclic ring that is aromatic or alicyclic, and n represents the degree of isomaleimide functionality, and is an integer of at least 2.

19. A polymaleamide comprising structural units of the formula

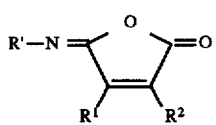

wherein

A is any polyvalent polymeric organic group and can include 0 to 100 heteroatoms that interrupt carbon chains, which group optionally can contain substituent groups, provided that A and its substituent groups do not interfere with formation of isomaleimides, polyisomaleimides, or polymers of the invention.

$R^1$ and $R^2$ are the same or different and are independently selected from the group consisting of hydrogen, $C_1$ to $C_{20}$ linear, branched or cyclic aliphatic groups, $C_6$ to $C_{20}$ aromatic groups, fluorine, chlorine, bromine, and iodine, or $R^1$ and $R^2$ can be joined together to form a cyclic ring that is aromatic or alicyclic.

and n is an integer of at least 2 representing the degree of functionality of A.

20. The polymaleamide according to claim 19 wherein said structural units comprise the formula:

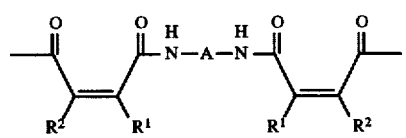

wherein

—HN—A—NH— is a polyvalent polymeric group derived from a primary polyamine by removal of at least one hydrogen atom from each primary amine group, $R^1$ and $R^2$ are the same or different and are independently selected from the group consisting of hydrogen, $C_1$ to $C_{20}$ linear, branched or cyclic aliphatic groups, $C_6$ to $C_{20}$ aromatic groups, fluorine, chlorine, bromine, and iodine, or $R^1$ and $R^2$ can be joined together to form a cyclic ring that is aromatic or alicyclic, and A is any polyvalent polymeric organic group and can include 0 to 100 heteroatoms that interrupt carbon chains, which group optionally can contain substituent groups, provided that A and its substituent groups do not interfere with formation of isomaleimides, polyisomaleimides, or polymers of the invention.

21. A polymer comprising the formula

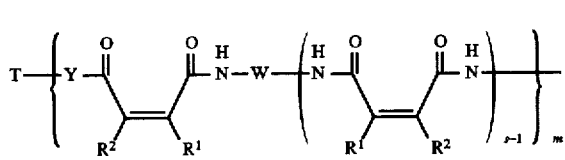

wherein Y is independently —HN—, —O—, or —S—,

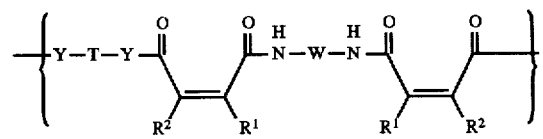

wherein W, Y, T, $R^1$, and $R^2$ are as previously defined, and each Y is independently selected.

23. A prepolymer comprising any of the formulae V, VI, and VIII:

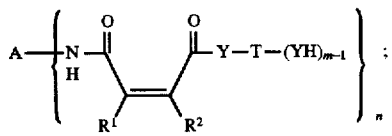     (V)

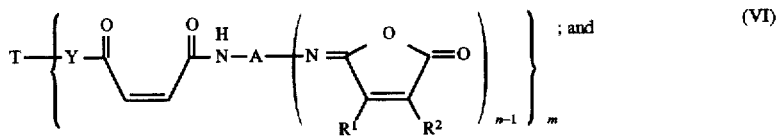     ; and     (VI)

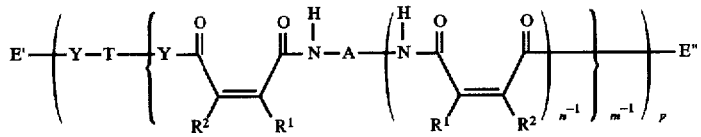

W is any polyvalent organic group that can include 0 to 100 heteroatoms that interrupt carbon chains, and optionally substituent groups, so long as W and its substituent groups do not interfere with formation of polyisomaleimides, polymaleamides, and polymers of the invention.

T is any polyvalent polymeric organic group and can include 0 to 100 heteroatoms that interrupt carbon chains, which group optionally can contain substituent groups, provided that T and its substituent groups do not interfere with formation of polymers of the invention.

$R^1$ and $R^2$ are the same or different and are independently selected from the group consisting of hydrogen, $C_1$ to $C_{20}$ linear, branched or cyclic aliphatic groups, $C_6$ to $C_{20}$ aromatic groups, fluorine, chlorine, bromine, and iodine, or $R^1$ and $R^2$ can be joined together to form a cyclic ring that is aromatic or alicyclic, and s and m independently are integers representing the degree of functionality of W and T, respectively.

22. The polymer according to claim 21 comprising repeating units of the formula:

where E' is H and E' is $—Y—T—(Y—H)_{m-1}$; or E' is

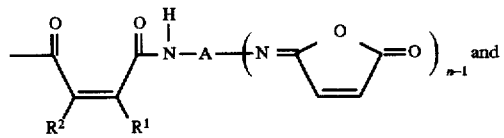

E" is

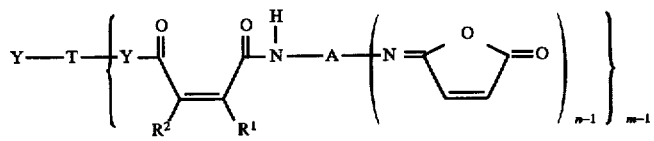

and wherein p is an integer of 2 or more and represents the degree of polymerization of the repeating unit, T is any polyvalent polymeric organic group and can include 0 to 100 heteroatoms that interrupt carbon chains, which group optionally can contain substituent groups, provided that T and its substituent groups do not interfere with formation of polymers of the invention, Y is independently —HN—, —O—, or —S—, A is any polyvalent polymeric organic group and can include 0 to 100 heteroatoms that interrupt carbon chains, which group optionally can contain substituent groups, provided that A and its substituent groups do not interfere with formation of isomaleimides, polyisomaleimides, or polymers of the invention, $R^1$ and $R^2$ are the same or different and are independently selected from the group consisting of hydrogen, $C_1$ to $C_{20}$ linear, branched or cyclic aliphatic groups, $C_6$ to $C_{20}$ aromatic groups, fluorine, chlorine, bromine, and iodine, or $R^1$ and $R^2$ can be joined together to form a cyclic ring that is aromatic or alicyclic, m is an integer representing the degree of functionality of T, and n represents the degree of isomaleimide functionality, and is an integer of at least 2, and each A and Y is independently selected.

* * * * *